US00PP09213P

United States Patent [19]

Trees

[11] Patent Number: Plant 9,213

[45] Date of Patent: Jul. 25, 1995

[54] NEW GUINEA IMPATIENS NAMED 'BFP-397 LIGHT SALMON'

[75] Inventor: Scott C. Trees, Arroyo Grande, Calif.

[73] Assignee: Geo. J. Ball, Inc., West Chicago, Ill.

[21] Appl. No.: 338,154

[22] Filed: Nov. 8, 1994

[51] Int. Cl.[6] ..... A01H 5/00
[52] U.S. Cl. ..... Plt./87.6
[58] Field of Search ..... Plt. 87.6

[56] References Cited

U.S. PATENT DOCUMENTS

P.P. 8,316 7/1993 Drewlow ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BFP-397 Light Salmon is provided. This new cultivar was the result of a controlled breeding program wherein a plant designated N2507-3 (non-patented in the United States) was pollinated by a plant designated 3616-A (non-patented in the United States). The new cultivar forms attractive very large, light salmon flowers with a white eye, displays an iridescent appearance, exhibits distinctive variegated medium green foliage, and possesses a medium growth habit. The new cultivar can be readily distinguished from the Cameo cultivar U.S. Plant Pat. No. 8,316).

1 Drawing Sheet

SUMMARY OF THE INVENTION

The present invention comprises a new and distinctive Impatiens plant, botanically known as New Guinea Impatiens, and hereinafter referred to by the cultivar name BFP-397 Light Salmon.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was a plant designated N2507-3 (non-patented in the United States) which exhibits bright salmon flowers and medium green variegated foliage. The male parent (i.e., the pollen parent) was a plant designated 3616-A (non-patented in the United States) which exhibits large rose pink flowers with dark green foliage and a vigorous growth habit. The parentage of the new cultivar can be summarized as follows:

N250-3×3616-A.

The seed resulting from the above pollination were sown and plantlets were obtained which were physically and biologically different from each other. Selective study resulted in the identification of a single plant of the new cultivar. This plant had large light salmon flowers and initially was designated BFP-397.

It was found that the new cultivar of the present invention (a) exhibits attractive very large light salmon flowers with a white eye,
(b) exhibits variegated medium green foliage,
(c) exhibits a good basal branching character, and
(d) exhibits a medium upright growth habit.

Asexual reproduction of the new cultivar by terminal or stem cuttings taken during 1993, at Arroyo Grande, Calif., U.S.A. has demonstrated that the characteristics of the new cultivar as herein described are firmly fixed and are retained throught successive generations of such asexual propagation.

The BFP-397 Light Salmon cultivar has not been observed under all possible environmental conditions to date. Accordingly, it is possible that the phenotype may vary somewhat with variations in the environment, such as temperature, light intensity, and day length.

When the new cultivar of the present invention is compared to the Cameo cultivar U.S. Plant Pat. No. 8,316), it is found that the new variety exhibits larger flowers, more flowers per branch, and a slightly less vigorous growth habit.

When plant material of the BFP-397 Light Salmon cultivar is subjected to standard random amplified polymorphic DNA marker analysis (RAPD) using a polymerase chain reaction (PCR) and a known unique set of DNA primers, it is found to exhibit a different fingerprint map when compared to that of the Cameo cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The color values were determined during the third week of July, 1994. The readings were taken between 9:00 and 10:00 a.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F.

during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Medium upright mounded. A mature plant commonly measures approximately 19 to 24 cm. in height and approximately 27 to 33 cm. in width. This can be compared to a height of approximately 23 to 25 cm. and a width of approximately 30 to 35 cm. for the Cameo cultivar.

*Foliage.*—The configuration is narrow and lanceolate. The leaves of the new cultivar commonly measure approximately 9.5 to 11.5 cm. in length and approximately 2.7 to 3.5 cm. in width. The foliage of the new cultivar is Green Group 137A (adaxial) and Green Group 137D (abaxial). Under high light conditions the foliage is Green Group 139A at the margins with variegation along mid-rib of Yellow Group 7A (adaxial) and Green Group 137D (abaxial). This can be compared with Green Group 137A (adaxial) and green Group 137D (abaxial), and under high light conditions, Green Group 137A at margins with variegation along mid-rib of Green-Yellow Group 1A (adaxial) and Green Group 137D (abaxial) for the Cameo cultivar. The stem of the new cultivar is Yellow-Green Group 145B. This can be compared to Yellow-Green Group 145C for the Cameo cultivar.

Flower description:

*Flowering habit.*—Freely flowering.

*Natural flowering season.*—Throughout the year in a greenhouse environment.

*Flowers borne.*—Above foliage arising from leaf axils.

*Flower color.*—Red Group 50C with eye of Red Group 56C formed adjacent the attachment points (adaxial) and Red Group 43D (abaxial). This can be compared to Red Group 51B with eye formed adjacent attachement points of 53D (adaxial) and Red Group 43C (abaxial) for the Cameo cultivar.

*Quantity of flowers.*—Approximately 9 to 11 per branch compared to 6 to 9 per branch for the Cameo cultivar.

*Number of petals.*—Five.

*Flower size.*—Approximately 7.0 to 7.7 cm. in length and approximately 6.6 to 7.0 cm. in width which can be compared to a length and widths of approximately 5.9 to 6.1 cm. for the Cameo cultivar.

*Nectary length.*—Approximately 5.0 cm. which can be compared to approximately 5.0 cm. for the Cameo cultivar.

*Nectary color.*—Red-Purple Group 60A which can be compared to Red Group 53D for the Cameo cultivar.

*Reproductive organs.*—The anthers are fused together forming one organ that surrounds the pistil. Generally, the anthers shed pollen prior to the stigma becoming receptive. The pollen color is Yellow-Orange Group 19D, the stigma color is Yellow-Green Group 144D, and the ovary color is Yellow-Green Group 144A for both the new cultivar and the Cameo cultivar.

I claim:

1. A new and distinct cultivar of New Guinea Impatiens named BFP-397 Light Salmon substantially as herein shown and described, which:

(a) exhibits attractive very large light salmon flowers with a white eye,
(b) exhibits variegated medium green foliage,
(c) exhibits a good basal branching character, and
(d) exhibits a medium upright growth habit.

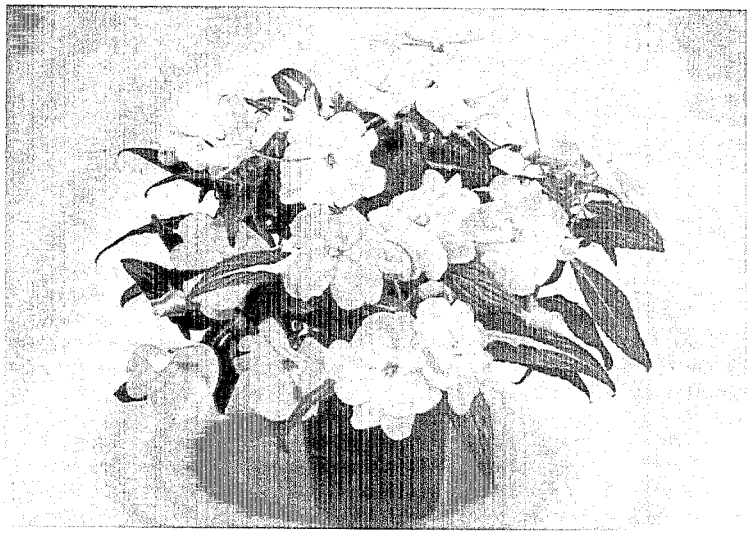

* * * * *